United States Patent [19]

Cousens et al.

[11] Patent Number: 4,510,245

[45] Date of Patent: Apr. 9, 1985

[54] ADENOVIRUS PROMOTER SYSTEM

[75] Inventors: Lawrence S. Cousens; Graeme I. Bell; Pablo D. T. Valenzuela, all of San Francisco, Calif.

[73] Assignee: Chiron Corporation, Emeryville, Calif.

[21] Appl. No.: 442,687

[22] Filed: Nov. 18, 1982

[51] Int. Cl.[3] .................... C12N 15/00; C12N 1/20; C12N 1/16; C12N 1/18; C12N 1/00; C12P 21/00; C12P 21/02; C12P 19/34; C07H 21/04

[52] U.S. Cl. .................... 435/172.3; 435/68; 435/70; 435/91; 435/253; 435/255; 435/256; 435/317; 536/27; 935/28; 935/34; 935/36; 935/37; 935/56

[58] Field of Search ............ 435/68, 70, 91, 172.3, 435/255, 256, 253, 317; 536/27

[56] References Cited

U.S. PATENT DOCUMENTS 4,387,162  6/1983  Aigle et al. .................... 435/255
4,430,428  2/1984  Fraser et al. .................... 435/68

OTHER PUBLICATIONS

Sentenac et al., in The Molecular Biology of the Yeast Saccharomyces, Strathern et al. (ed.), Cold Spring Harbor Laboratories, 1982, pp. 589–592.
Beggs et al., Nature 283, 835, (1980).
Dobson et al., *Nucl. Acids, Res.*, (1982), 10:2625–2637.
Kiss et al., *J. Bacteriol.*, (1982), 150:465–470 and 149:542–547.
Klenow et al., *Proc. Natl. Acad. Sci.*, (1970), 65:168–175.
Maxam et al., *Proc. Natl. Acad. Sci. USA*, (1977), 74:560–564.
McKnight et al., *Science*, (1982), 217:316–324.
Rosenberg et al., *Ann. Rev. Genet.*, (1979), 13:319–353.
Valenzuela et al., *Nature*, (1982), 298:347–350.
Weil et al., *Cell*, (1979), 18:469–484.

Primary Examiner—Thomas G. Wiseman
Assistant Examiner—James Martinell
Attorney, Agent, or Firm—Bertram I. Rowland

[57] ABSTRACT

The adenovirus major late promoter is employed as a promoter for expression in a yeast host. Constructions are provided for expression in yeast with the adenovirus major late promoter and a coding segment.

6 Claims, 4 Drawing Figures

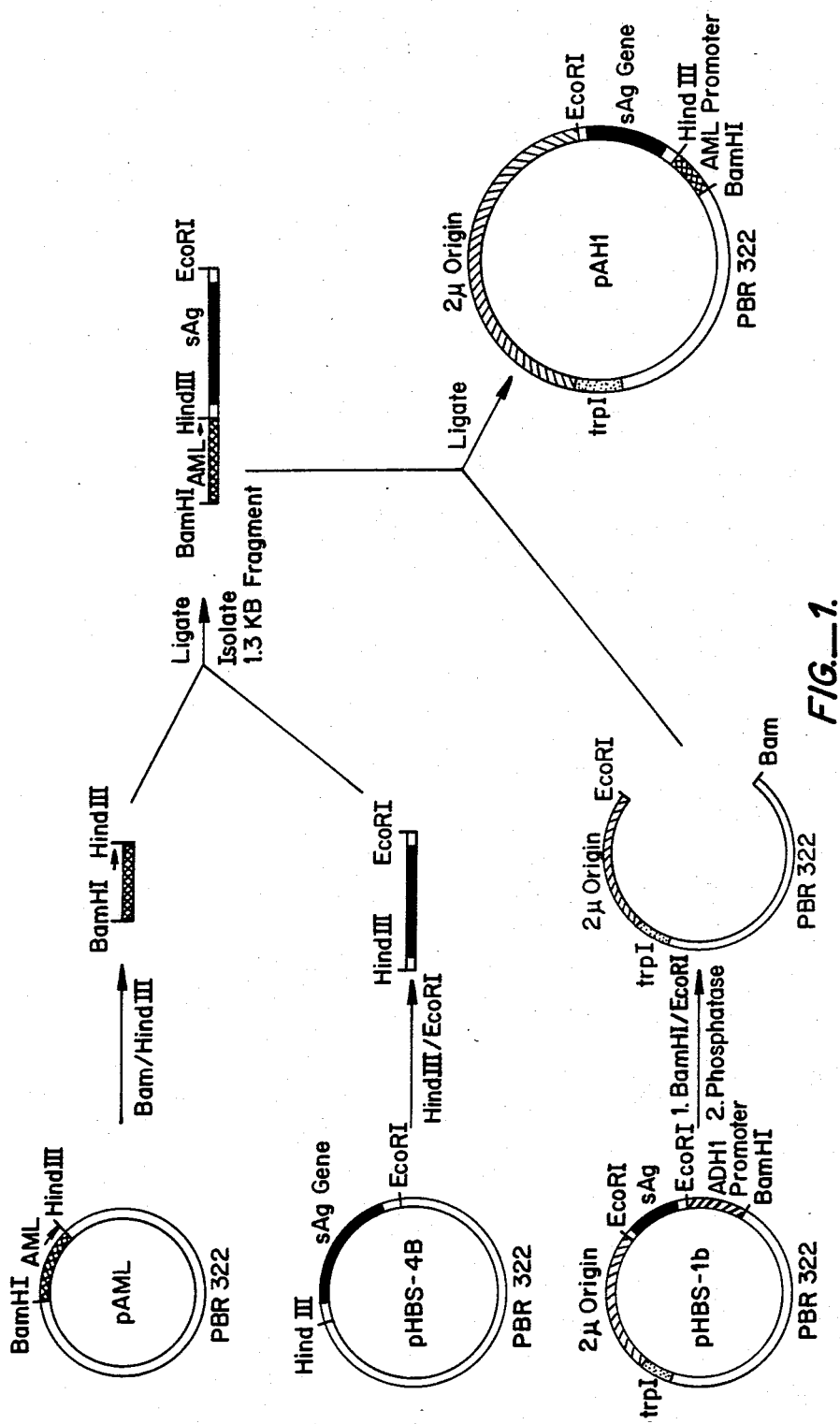
FIG._1.

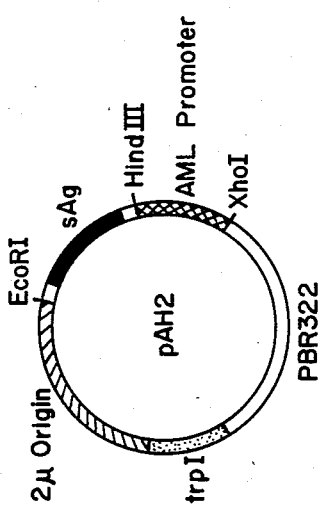
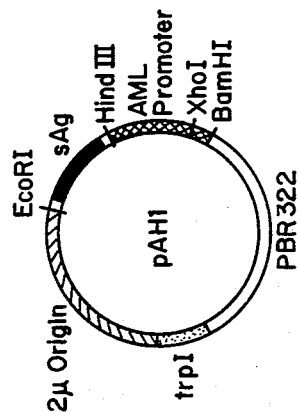
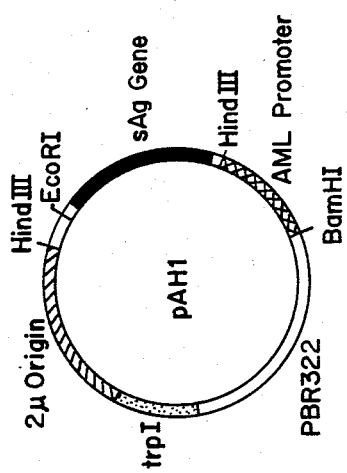
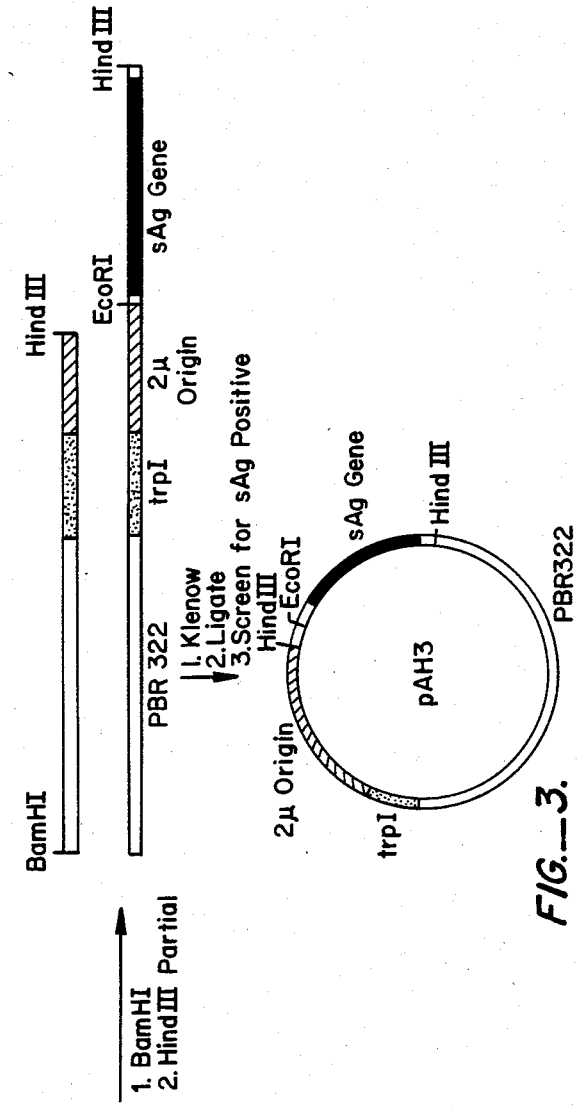
FIG.—2.
FIG.—3.

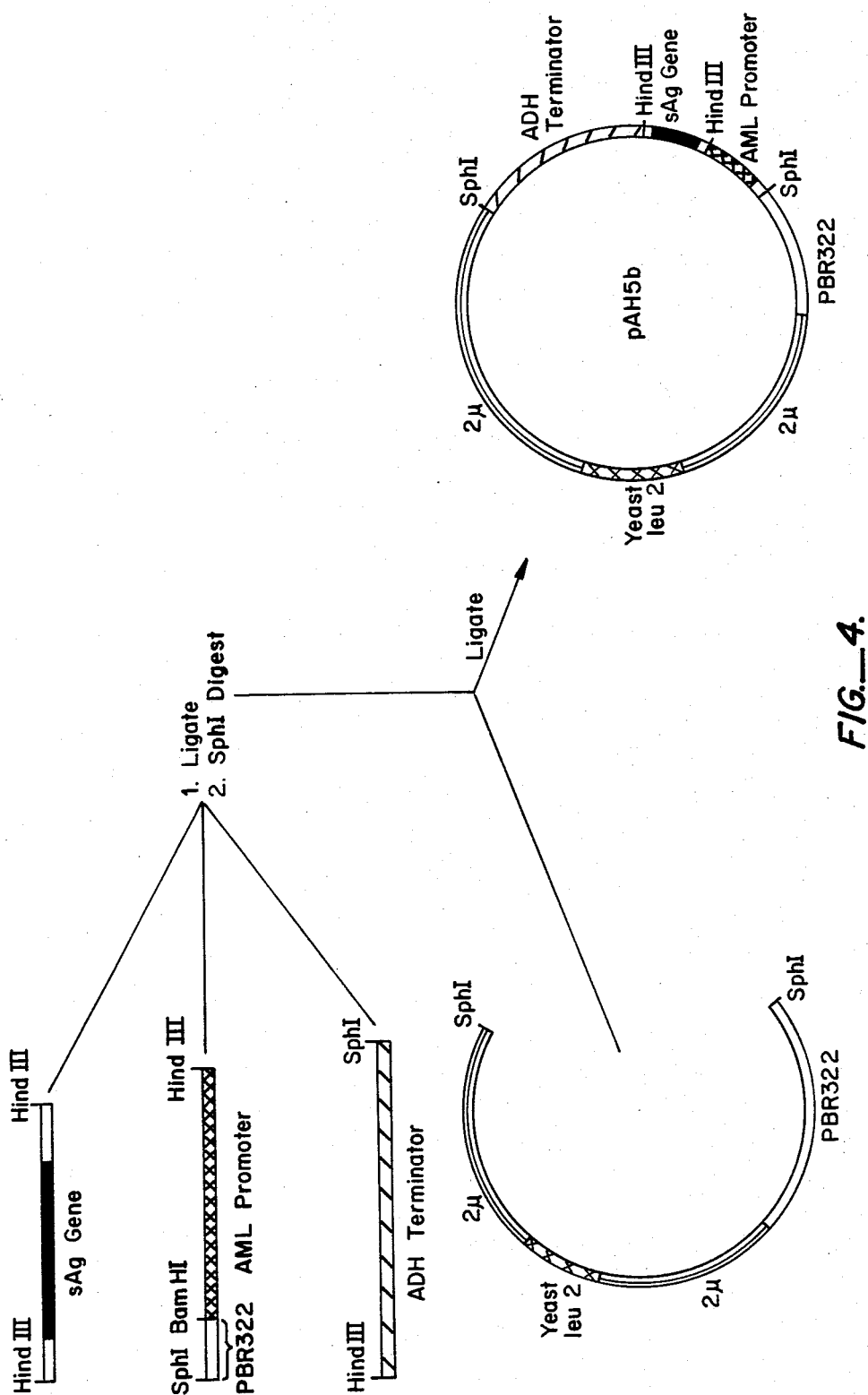
FIG._4.

ADENOVIRUS PROMOTER SYSTEM

BACKGROUND OF THE INVENTION

The present invention relates to a development of recombinant expression vectors useful for the expression of DNA coding segments in yeasts, fungi and mammalian cells, and to the development of shuttle expression vectors, capable of expressing a DNA coding segment in both yeasts and mammalian cells. The vector system herein described employs an adenovirus promoter to control expression of the inserted DNA coding segment. The described promoter system was not previously known to be functional in non-mammalian cells.

The adenoviruses constitute a class of viruses infective to animals, including humans, and known to transform infected mammalian cells in culture with low frequency. The adenoviruses have been extensively studied and are well-characterized. The DNA nucleotide sequences are known for specific strains. (For general background, see Tooze, J., *Molecular Biology of Tumor Viruses, Part II: DNA Tumor Viruses,* Cold Spring Harbor Laboratory, Cold Spring Harbor, New York (1980). Genetically, the functions of the virus are classified as "early" or "late," depending on whether they are expressed before or after the onset of viral DNA synthesis in the infection cycle. Early functions are expressed under control of several early promoters. In contrast, the majority of late functions are expressed under the control of a single, very active, promoter known as the adenovirus major late promoter (herein AML promoter). The nucleotide sequence of the AML promoter has been published, Tooze, supra. Comparison with the known nucleotide sequences of active yeast promoters reveals few points of similarity between the AML promoter and yeast promoters, other than certain short segments which appear to be characteristic of almost all eukaryotic promoters. By contrast, many points of structural similarity are known, between the yeast promoters for alcohol dehydrogenase (ADH) and glyceraldehyde phosphate dehydrogenase (GAPDH). [See Dobson, M. J., et al., Nucl. Acids Res. 10, 2625 (1982)].

A promoter is defined herein as a DNA segment capable of functioning to initiate transcription of an adjoining DNA segment. Transcription is the synthesis of RNA (herein termed messenger RNA, or mRNA), complementary to one strand of the DNA adjoining the promoter region. In eukaryotes, mRNA synthesis is catalyzed by an enzyme termed RNA polymerase II. The minimum essential elements of promoter function are two: to provide a starting point for the initiation of transcription and to provide a binding site for RNA polymerase II near the start site permitting selection of the proper strand of DNA as a template for mRNA synthesis. In addition, a eukaryotic promoter functions to regulate the relative efficiency of transcription of coding segments under its control. An active promoter is one which induces the synthesis of relatively large amounts of mRNA complementary a strand of the adjacent DNA coding segment.

The structural correlates of promoter function have not been clearly established. A promoter segment can be identified in nature as a region lying adjacent to a given structural gene at its 5' end. (References to the 5' and 3' ends of a gene will be understood to indicate the corresponding respective ends of mRNA transcribed therefrom, and these, in turn, will be understood to correlate with the $NH_2$— and —COOH termini of the encoded protein, respectively. Mutations in the 5' untranslated region, adjacent to a coding segment of DNA, and extending from 200 to 400 nucleotides from the start codon thereof, display a variety of functional defects in transcription, ranging from reduced rate or efficiency of transcription, to total cessation of transcription. Where several genes are transcribed together in a single transcription unit, such mutations can result in the simultaneous loss or reduction in amount of several gene products. Such mutations define the promoter region for the structural gene or genes they affect. Comparisons of nucleotide sequences of promoters of various genes from various species have revealed only a few short regions of nucleotide sequenced similarity in common between them. Most notable of these is the "TATA box," a segment of about five to ten nucleotides located generally about 70 to 230 nucleotides upstream from the start of a coding segment, having a sequence generally resembling TATAA. For a review of structural comparisons, see Rosenberg, M. et al., Ann. Res. Genetics, 13, 319 (1979). The TATA box is believed to function in the initiation of transcription. Other examples of short regions of sequence similarity having similar locations in a number of promoters, include segments with such whimsical descriptors as "CAAT BOX," and "CACA BOX,". However, many promoters lack one or more of these features and their function is not established.

Comparative studies of the effects of promoter mutations lying distal to the start of the coding segment have been undertaken, e.g., by McKnight, S., et al., Science 217, (1982). Such studies have shown, in general, that certain regions lying upstream from the TATA box appear to be involved in the binding and orientation of the RNA polymerase to the DNA segment to be transcribed. Structural variations in this portion of the promoter presumably affect the efficiency of transcription and are known to vary substantially from one species to another.

The structures of over a dozen yeast promoters have been determined and the structures were compared by Dobson, M. J. et al., Nucleic Acids Research 10, 2625 (1982). The yeast promoters have many points of similarity not shared by non-yeast promoters, such as the adenovirus major late promoter (supra, Tooze et al.), and herpes virus thymidine kinase gene (Kiss, G., et al., J. Bact. 149, 542, 1982; Kiss, G., et al., J. Bact. 150, 465 (1982). Further, it has been shown (Kiss, G. et al., supra) that the thymidine kinase promoter of herpes virus does not function in yeast.

The present invention stems from the surprising discovery that the major late promoter of adenovirus is functional and highly active in yeast. That discovery has made it possible to construct, for the first time, expression vectors for the expression of DNA coding segments in yeast, controlled by the AML promoter, and for methods of synthesizing proteins in yeast cells transformed by such vectors.

The construction of vectors suitable for the expression of a DNA coding segment in yeast has been described, see, e.g., Ammerer, G. et al., *Recombinant DNA, Proc. 3rd Cleveland Symp. Macromolecules* (Walton, A. G., ed.), p. 185, Elsevier, Amsterdam (1981). Shuttle vectors, capable of replication either in a bacterial strain such as *Escherichia coli* and in yeast have been described. However, such vectors have relied upon the use of known yeast promoters for expression in yeast. Previously described shuttle vectors have been limited to one of the alternative hosts for expression. For example, shuttle vectors having yeast promoters are limited to expression of the DNA coding sequence in yeast only. A disadvantage of such vectors is that an extensive region of yeast homology, the promoter region, provides an opportunity for genetic recombination between the vector and the yeast chromosome, possibly resulting in integration of the vector. Consequently, the copy number per cell of sequences represented by the vector is one per chromosome. The reduction in copy number makes it impossible to achieve the highest levels of expression.

Expression vectors for yeast, containing the AML promoter, provide distinct advantages over vectors previously available in the art. In addition to promoting a high level of expression of any DNA coding sequence under AML promoter influence, such vectors, according to the present invention, lack the regions of DNA homology between vector and chromosome provided by prior art vectors employing a yeast promoter. In fact, vectors lacking any homology with yeast chromosomal DNA can be constructed, using a replication origin provided by yeast two micron circle plasmid DNA. Furthermore, the discovery of a promoter functional in both yeast and mammalian cells makes possible the construction of shuttle vectors capable of expressing a DNA coding sequence in either host. Therefore, the present invention makes possible, for the first time, the construction of true expression shuttle vectors.

SUMMARY OF THE INVENTION

The invention is based upon the surprising discovery that the major late promoter of adenovirus (hereinafter the AML promoter) functions in yeast to provide high efficiency transcription and translation of a DNA segment coding for a protein. This discovery makes possible the construction of expression vectors, such as plasmids, containing a desired DNA coding segment, which vector is able to replicate in yeast, providing multiple copies per cell, and which coding segment is expressed in yeast cells transformed by the vector. The combination of AML promoter and DNA coding segment may be placed within a vector capable of replicating in both yeast and mammalian cells, to provide an expression shuttle vector between yeast and mammalian cells. Expression of the DNA coding segment in such a vector takes place in either host cell. Alternatively, the AML promoter-DNA coding segment unit may be transferred to a vector capable of replication in mammalian cells, thereby providing for expression of the coding segment in the mammalian cell. It is even feasible to construct triple shuttle vectors, capable of replication in a bacterial host, a yeast, or a mammalian host, capable of expression in both the yeast and mammalian hosts.

It follows from the discovery that the AML promoter functions in yeast that there are many other organisms similar to yeast in which the AML promoter can be shown to function. Such organisms include, by way of example, and without limitation, other members of the genus Saccharomyces, members of the genus Aspergillus, and members of the genus Neurospora. The screening of organism strains suitable for use with the AML promoter can be accomplished according to the teachings herein, without undue experimentation. In addition, it will be understood that any of the many strains of adenovirus, whether infective to humans or other animals, may be employed as the source for the AML promoter sequence. It is deemed preferable to employ a virus strain that is non-oncogenic.

The principles for construction of a vector having proper orientation and juxtaposition of the promoter sequence and coding segment with respect to each other are matters well known to those skilled in the art. For example, such minimal conditions for operativeness as the existence of a start codon in the DNA coding segment, at its beginning, and location of the promoter segment proximal to the 5' end of the coding segment, are matters deemed within the scope of knowledge of those skilled in the art. The DNA coding segment may be any DNA segment from which, as a minimum, an RNA transcript is to be made. In many instances, translation of the RNA transcript will be desired, and in such circumstances, it will be understood that the coding segment will include nucleotide sequences providing the necessary signals to provide RNA processing and translation. The coding segment may comprise cDNA, genomic DNA and synthetic DNA.

BRIEF DESCRIPTION OF THE DRAWINGS

FIG. 1 is a schematic diagram of the construction of pAH1.

FIG. 2 shows the synthesis and structure of pAH2.

FIG. 3 shows the construction and structure of pAH3.

FIG. 4 shows the construction and structure of pAH56.

DETAILED DESCRIPTION OF THE INVENTION

Construction of a yeast vector comprising the AML promoter of adenovirus 2 is described in detail to provide an example of the invention. The use of a yeast vector comprising the AML promoter for the expression of hepatitis B surface antigen coding segment under the influence of the AML promoter is demonstrated. Two promoter constructions are shown, one having a somewhat shorter nucleotide sequence than the other. Nucleotide sequences at the 5' end of the promoter sequence (in the same orientation as the coding segment), tend to be less significant for promoter function than sequences closer to the translational start point. However, for maximum promoter activity, the AML promoter sequence should include approximately 200–300 nucleotides, counting from the initiation point of translation.

EXAMPLE 1

Construction of a Yeast Vector Comprising the AML Promoter

The SmaF fragment of adenovirus 2, which contains a region previously identified as the major late promoter, was isolated and purified as described by Weil et al. Cell, 18, 469 (1979). The fragment was cloned in the vector in pBR313, and amplified in amount by multiple cycles of growth in an *E. coli* host. (The techniques used herein of restriction endonuclease digestion, ligation, transformation, gel electrophoresis, isolation and purification of plasmid DNA were standard techniques known in the art unless otherwise specified. Detailed descriptions of such techniques are found, for example, in *Methods of Enzymology*, Vol 68, R. Wu, Ed., 1980. (The AML promoter segment was reisolated by SmaI digestion of the plasmid into which it was initially cloned, and further digested with Pvu II. Decameric, HindIII linkers (commercially available from Collaborative Research, Inc., Waltham, Mass.) were attached to the ends by a DNA ligase-catalyzed reaction. The material was then digested with HindIII endonuclease and a fragment of about 1150 base pairs was identified and isolated by gel electrophoresis. That fragment was digested with Alu I endonuclease, generating a single blunt end, resulting from Alu I endonuclease cleavage. An oligonucleotide BamHI linker was attached by blunt end ligation. The end not affected by the Alu I digestion was similarly unaffected by the ligation, because the previous HindIII endonuclease digestion did not generate a blunt end to which the BamHI oligonucleotide linker could be joined. After BamHI endonuclease digestion, the resulting fragment, now approximately 440 base pairs length, was isolated by gel electrophoresis and inserted into pBR327 previously digested with BamHI and HindIII endonucleases. Transformants were screened for the existence of a fragment of about 440 base pairs produced by combined digestion with BamHI and HindIII endonucleases. Positive clones were confirmed by nucleotide sequence analysis, using the technique of Maxam, A., et al., Proc. Nat. Acad. Sci. USA 74, 560 (1977).

The sequence analysis confirmed that the 440 base pair fragment contained the AML promoter. Orientation of the promoter sequence was such that the transcription initiation site was nearest the HindIII end of the fragment and farthest from the BamHI end of the fragment.

The DNA coding segment used to demonstrate expression was a fragment containing a nucleotide sequence coding for the hepatitis B surface antigen. The coding segment was previously described in copending application Ser. No. 402,330, obtained by combined digestion with HindIII and EcoRI endonucleases of the plasmid pHBS-5 described therein.

The plasmid pHBS-5 was digested with EcoR1 endonuclease generating a fragment of approximately 850 base pairs including the S-protein coding region and flanking 3'-and 5'-untranslated regions, terminated by EcoR1 linker oligonucleotide segments. The HBV-DNA segment was reisolated by preparative gel electrophoresis, electroeluted and divided into samples which were digested with the exonuclease Bal-31 for varying times from 0.5 to 30 minutes at 37° C. The extent of exonuclease digestion was characterized qualitatively by digesting a portion of each sample with XbaI endonuclease. The surface antigen coding region contains an XbaI site beginning 92 base pairs from the first base of the start codon. Therefore, samples in which Bal-31 digestion had proceeded beyond the Xba1 site would yield only one fragment upon gel electrophoresis after XbaI endonuclease incubation while samples with fewer bases removed would yield two classes of fragment: a homogenous large fragment and a heterogeneously sized small fragment. Samples yielding only one XbaI fragment were discarded. Samples yielding two size classes of fragments were blunt-ended by incubation with DNA polymerase I (Klenow fragment, see Klenow, H., et al., Proc. Nat. Acad. Sci. 65, 168 (1970) in the presence of all four deoxynucleotide triphosphates. Linker oligonucleotides containing the HindIII recognition site were added by blunt-end ligation using T4 DNA ligase. HindIII specific cohesive ends were generated by digestion with HindIII endonuclease. The mixture of fragments was then digested with XbaI endonuclease and fractionated by gel electrophoresis. Fractions of approximately 90–110 nucleotides length were isolated from the gel and joined by ligation to pHBS-5 previously cut with HindIII and XbaI endonucleases. *E. coli* transformants were screened for tetracycline sensitivity. Clones were further screened for the presence of plasmid DNA yielding HindIII-XbaI fragments of about 90–110 nucleotides length. The largest of these (about 110 nucleotides) was chosen. The HindIII specific end of the fragment was located proximal to the start codon of the surface antigen coding segment, on the 5' side thereof. Consequently, the AML promoter fragment and surface antigen coding segment could be joined in correct orientation to one another by virtue of the complementarity of their respective HindIII-specific ends.

A mixture of the approximately 440 base pair AML promoter fragments and the surface antigen coding segment was treated with DNA ligase under reaction conditions favorable to the DNA joining reaction. The ligation mixture was then digested with a mixture of BamHI and EcoR1 endonucleases, to separate concatamers arising from self-ligation at the BamHI and EcoR1 sites. The mixture was then fractionated by gel electrophoresis, and a fragment of about 1300 base pairs was isolated as the main reaction product.

The 1300 base pair composite fragment, designated the AML-HBsAg gene, was inserted into the plasmid vector pHBS16, previously described in copending application Ser. No. 402,330. The plasmid, and a microorganism transformed thereby, were placed on deposit with the ATCC on Aug. 4, 1981, and have accession Numbers 40,043 and 20,619 for the plasmid and microorganism, respectively. The plasmid pHBS16 was digested with EcoR1 and BamHI endonucleases and the largest fragment resulting therefrom was reisolated by gel electrophoresis. The large pHBS16 fragment was joined with the AML-HBsAg gene, using DNA ligase, and the resulting plasmid was used to transform *E. coli* HB101. The transformants were screened to identify those yielding the correctly sized fragments following digestion with EcoR1, BamHI and HindIII endonucleases. The resulting plasmid was designated pAH1. A schematic diagram of the construction of pAH1 is shown in FIG. 1.

A second plasmid was constructed by modification of pAH1. The modification consisted of deleting a segment of about 150 nucleotides length, well upstream from the TATA box at the 5' end of the promoter fragment. Plasmid pAH1 was then digested with BamHI and XhoI endonucleases. The resuling single-stranded ends were filled in, using the Klenow fragment of DNA polymerase. The reaction mixture was diluted to minimize the likelihood of intermolecular ligation, and treated with DNA ligase to regenerate closed loop DNA by blunt end ligation. The nucleotide sequences of the BamHI and XhoI, cleaved and blunt-ended as described, are such that, when joined together, they regenerate a complete XhoI site.

The resulting plasmid was designated pAH2. Its route of synthesis and structure are shown schematically in FIG. 2.

A third vector was constructed, as a control, by deleting the AML promoter region from plasmid pAH1. If expression of the surface antigen in pAH1 was, in fact, controlled by the AML promoter, deletion of the promoter should result in loss of expression.

The plasmid pAH1 was digested with BamHI endonuclease, and then partially digested with HindIII endonuclease. Since digestion of both HindIII sites of pAH1 would result in excision of the surface antigen coding region, a partial digestion was necessary, the desired result being a single cleavage at the HindIII site joining the surface antigen coding region and the AML promoter. After partial digestion, the unpaired ends were filled in with the Klenow fragment of DNA polymerase. The reaction mixture was diluted to enhance the probability of intramolecular ligation, and closed loop DNA was regenerated by blunt end ligation. Plasmids initially cleaved at the desired HindIII site resulted in a larger closed loop DNA than those cleaved at the undesired site, or at both sites. After identifying the correctly cleaved plasmid by gel electrophoresis, these were further screened for a subset containing a new, second HindIII site. The existence of a subset having a new HindIII site was discovered to have occurred as a result of partial exonuclease activity of the DNA polymerase preparation. When two base pairs are removed from the BamHI end, in the blunt end reaction using the DNA polymerase Klenow fragment, subsequent blunt end ligation regenerates a HindIII site near the 5' end of the surface antigen coding segment. A schematic of the construction and structure of the resulting plasmid, pAH3, is shown in FIG. 3.

A fourth vector was constructed, to incorporate a terminator region adjacent to the 3' end of the coding segment. For this purpose, the AML promoter fragment was derived and purified from pAH1 digested with HindIII endonuclease and SphI endonuclease. The hepatitis B surface antigen coding segment was a TacI-HpaI fragment of hepatitis B virus DNA, obtained as described by Valenzuela, P., et al., Nature 298, 347 (1982). The surface coding antigen fragment was then modified by the addition of HindIII linkers at each end, by blunt end ligation. The ADH terminator region of the yeast ADH gene was a HindIII-SphI fragment prepared as described in copending application Ser. No. 402,330, supra. The specificity of the resulting ends made it possible to join the promoter, coding region and terminator to form a single composite, DNA segment herein termed the surface antigen cassette. After the three fragments were joined by DNA ligase, the reaction product was treated with SphI endonuclease to destroy dimers and concatamers incorrectly joined at the SphI sites. After gel electrophoresis to isolate and purify the cassette DNA, the cassette was joined with plasmid pHBS56 digested with endonuclease. The plasmid pHBS56 has been described in copending application Ser. No. 402,330, supra, and, together with a yeast strain transformed thereby, has been placed on deposit with ATCC on July 7, 1982, accession numbers 40,047 and 20,648, for the plasmid and yeast strain, respectively. The cassette DNA was joined to the cut plasmid by DNA ligase and the resulting plasmid, termed pAH56, was used to transform yeasts, after screening for clones having the predicted restriction site pattern. Details of construction and structure of pAH56 are shown schematically in FIG. 4. The orientation of the cassette shown in the diagram is arbitrary; however, since the cassette is self-contained with respect to the elements necessary for expression of the coding region contained therein, it makes no difference, so far as function is concerned, which orientation was isolated, since both are functional.

The structures of 5' untranslated region in pAH1 and pAH56 are shown in Tables 1 and 2, respectively, based on nucleotide sequence analysis. The sequence also shows the 5' end of the surface antigen coding segment, up to the XbaI site. The sequence for pAH2 is identical to the sequences shown, except that the first approximately 150 nucleotides of the sequence, up to the XhoI site, are deleted in pAH2. The sequence differs at two points from the published sequence for the AML promoter, at position 204, where the published sequence shows an AT pair instead of the GC pair, found in the present study, and at position 339, where the published sequence shows a GC pair, and the present results indicate an AT pair. The TATA box begins at about position 381, and has the sequence TATAAAA. The cap site, where transcription is initiated in mammalian cells, is the AT pair at position 412. The start codon of the coding sequence is the ATG sequence, which commences at position 464. In pAH56, the start codon is the ATG triplet commencing at position 481.

EXAMPLE 2

Expression in Yeast Mediated by the AML Promoter
Yeast cells transformed with either pAH56, pAH1 or pAH3, were grown in 100 ml cultures at 30° C. in YEPD medium. The host cell strain for pAH56 was S. cerevisiae 2150-2-3, and for pAH1 and pAH3, the host cell strain was S. cerevisiae AB35-14D, as previously described in copending application Ser. No. 402,330.
The total protein concentration was determined by spectrophotometric measurement of coomassie blue dye binding. The surface antigen concentration was determined by radioimmunoassay, using a commercially available assay kit (Abbott Laboratories, North Chicago, Ill.). The results are shown in Table 3.
The pAH56 vector produced about ten times the surface antigen expressed under the influence of the pAH1 vector. However, no radioimmunoassay-detectable surface antigen was produced by pAH3, the vector lacking the AML promoter. For comparison, the amount of antigen produced with the AML promoter, in vector pAH1, was about 80% of the amount produced by the corresponding vector having a yeast ADH promoter. Therefore, it can be seen that the AML promoter is highly active in yeast, and that the expression observed with pAH1 and pAH56 is due to the presence of the AML promoter in the vector, and not due to some other, outlying promoter.

While the invention has been described by reference to specific operating examples, it is intended that the scope of the invention shall include such alternative embodiments and variations as lie within the grasp of those ordinarily skilled in the art, or combined with expedients known in the art.

TABLE 1

```
     BamhlSau3a      Cfrl              EcorllScrFl
1 GGATCCGGCTCTGGCCGTTCGGGGTCAAAAACCAGGTTTCCCCCATGCTTTTTGATGCGT
  CCTAGGCCGAGACCGGCAAGCCCCAGTTTTTGGTCCAAAGGGGGTACGAAAAACTACGCA
  Xho2Hpall      Haelll                Apyl
```

TABLE 1-continued

```
              Mnll             Hpall               Hph
 61 TTCTTACCTCTGGTTTCCATGAGCCGGTGTCCACGCTCGGTGACGAAAAAGGCTGTCCGT
    AAGAATGGAGACCAAAGGTACTCGGCCACAGGTGCGAGCCACTGCTTTTTCCGACAGGCA AccI          MnllStul       MnllPaeR7ITaqI    Sac2AsulMnll
121 GTCCCCGTATACAGACTTGAGAGGCCTGTCCTCGAGCGGTGTTCCGCGGTCCTCCTCGTA
    CAGGGGCATATGTCTGAACTCTCCGGACAGGAGCTCGCCACAAGGCGCCAGGAGGAGCAT
                         HaelHaelll     AvalXhol        TacIAva2    Mnll Ava2      Ddel           TacI    ApylEcorllHaelll    MnllDdel
181 TAGAAACTCGGACCACTCTGAGACGAAGGCTCGCGTCCAGGCCAGCACGAAGGAGGCTAA
    ATCTTTGAGCCTGGTGAGACTCTGCTTCCGAGCGCAGGTCCGGTCGTGCTTCCTCCGATT
               AsuI                      HgalScrFlHael Mnll                          Ava2           ApylScrFl   Mboll     N
241 GTGGGAGGGGTAGCGGTCGTTGTCCACTAGGGGGTCCACTCGCTCCAGGGTGTGAAGACA
    CACCCTCCCCATCGCCAGCAACAGGTGATCCCCCAGGTGAGCGAGGTCCCACACTTCTGT
                                             AsuI         EcorII spCI    Mnll              Hph                           Hael         Hp
301 CATGTCGCCCTCTTCGGCATCAAGGAAGGTGATTGGTTTATAGGTGTAGGCCACGTGACC
    GTACAGCGGGAGAAGCCGTAGTTCCTTCCACTAACCAAATATCCACATCCGGTGCACTGG
         MbolI                                              Haelll     Nc ScrFl                                Hhal       Mnll     Mboll
361 GGGTGTTCCTGAAGGGGGGCTATAAAAGGGGGTGGGGGCGCGTTCGTCCTCACTCTCTTC
    CCCACAAGGACTTCCCCCCGATATTTTCCCCCACCCCCGCGCAAGCAGGAGTGAGAGAAG
    iI                                              TacI MnllHaelll    HindIII    Hph
421 CGCATCGCTGTCTGCGAGGGCCAGCCAAGCTTGGGTGACGAACATGGAGAACATCACATC
    GCGTAGCGACAGACGCTCCCGGTCGGTTCGAACCCACTGCTTGTACCTCTTGTAGTGTAG
                   AsuI         AluI Hinfl     Ava2                              HindII   Hinfl
481 AGGATTCCTAGGACCCCTGCTCGTGTTACAGGCGGGGTTTTTCTTGTTGACAAGAATCCT
    TCCTAAGGATCCTGGGGACGAGCACAATGTCCGCCCCAAAAAGAACAACTGTTCTTAGGA
            Avr2AsuI                                               Mnl Hinfl
541 CACAATACCGCAGAGTCTAGA
    GTGTTATGGCGTCTCAGATCT
    i            Xbal
```

TABLE 2

```
    BamhlSau3a        Cfrl               EcorllScrFl
  1 GGATCCGGCTCTGGCCGTTCGGGGTCAAAAACCAGGTTTCCCCCATGCTTTTTGATGCGT
    CCTAGGCCGAGACCGGCAAGCCCCAGTTTTTGGTCCAAAGGGGGTACGAAAAACTACGCA
    Xho2Hpall    Haelll                     ApyI Mnll            Hpall              Hph
 61 TTCTTACCTCTGGTTTCCATGAGCCGGTGTCCACGCTCGGTGACGAAAAAGGCTGTCCGT
    AAGAATGGAGACCAAAGGTACTCGGCCACAGGTGCGAGCCACTGCTTTTTCCGACAGGCA AccI          MnllStul       MnllPaeR7ITaqI    Sac2AsulMnll
121 GTCCCCGTATACAGACTTGAGAGGCCTGTCCTCGAGCGGTGTTCCGCGGTCCTCCTCGTA
    CAGGGGCATATGTCTGAACTCTCCGGACAGGAGCTCGCCACAAGGCGCCAGGAGGAGCAT
                         HaelHaelll     AvalXhol        TacIAva2    Mnll Ava2      Ddel           TacI    ApylEcorllHaelll    MnllDdel
181 TAGAAACTCGGACCACTCTGAGACGAAGGCTCGCGTCCAGGCCAGCACGAAGGAGGCTAA
    ATCTTTGAGCCTGGTGAGACTCTGCTTCCGAGCGCAGGTCCGGTCGTGCTTCCTCCGATT
               AsuI                      HgalScrFlHael Mnll                          Ava2           EcorllScrFl  Mboll
241 GTGGGAGGGGTAGCGGTCGTTGTCCACTAGGGGGTCCACTCGCTCCAGGGTGTGAAGACA
    CACCCTCCCCATCGCCAGCAACAGGTGATCCCCCAGGTGAGCGAGGTCCCACACTTCTGT
                                             AsuI         ApyI NspCI    Mnll              Hph                           Hael         Nc
301 CATGTCGCCCTCTTCGGCATCAAGGAAGGTGATTGGTTTATAGGTGTAGGCCACGTGACC
    GTACAGCGGGAGAAGCCGTAGTTCCTTCCACTAACCAAATATCCACATCCGGTGCACTGG
         MbolI                                              Haelll     Hp ScrFl                                Hhal       Mnll     Mboll
361 GGGTGTTCCTGAAGGGGGGCTATAAAAGGGGGTGGGGGCGCGTTCGTCCTCACTCTCTTC
    CCCACAAGGACTTCCCCCCGATATTTTCCCCCACCCCCGCGCAAGCAGGAGTGAGAGAAG
    all                                             TacI MnllHaelll    HindIII     Mnll      Ava2
421 CGCATCGCTGTCTGCGAGGGCCAGCCAAGCTTGGCGAGGACTGGGGACCCTGTGACGAAC
```

TABLE 2-continued

```
    GCGTAGCGACAGACGCTCCCGGTCGGTTCGAACCGCTCCTGACCCCTGGGACACTGCTTG
                     Asul      Alul                Asul Hinfl    Asul
481 ATGGAGAACATCACATCAGGATTCCTAGGACCCCTGCTCGTGTTACAGGCGGGGTTTTTC
    TACCTCTTGTAGTGTAGTCCTAAGGATCCTGGGGACGAGCACAATGTCCGCCCCAAAAAG
                         Avr2Ava2

HindlI    Hinfl                   Hinfl
541 TTGTTGACAAGAATCCTCACAATACCGCAGAGTCTAGA
    AACAACTGTTCTTAGGAGTGTTATGGCGTCTCAGATCT
            Mnll                        Xbal
```

TABLE 3

Expression of Surface Antigen in Yeast

One hundred milliliter cultures of the genetically engineered yeast, i.e., containing the 56-type plasmid, were grown in leucine deficient medium, at 30° C. A cell free lysate was prepared by agitation with glass beads. The protein concentration was determined by the coomassie dye binding method. The surface antigen concentration was determined with the Abbott radioimmunoassay kit.

| Expt. # | Protein Concentration (mg/ml) | sAntigen Concentration (μg/ml) | Specific (μg Ag) Activity (mgPtn) |
|---|---|---|---|
| 1 | 25 | 10.2 | 0.41 |
| 2 | 38 | 12.5 | 0.38 |
| 3 | 17 | 5.7 | 0.33 |
| 4 | 17 | 5.8 | 0.34 |
| Average | 24 | 8.6 | 0.37 |

We claim:

1. A yeast expression vector comprising a replication origin functional in yeast and a DNA coding segment and an adenovirus major late promoter segment adjacent to the 5' end of the coding segment, the promoter segment being oriented so as to initiate transcription of the coding segment.

2. The expression vector of claim 1, comprising additionally a bacterial replication origin and being capable of being replicated in bacteria.

3. The vector of claim 1 or 2, comprising additionally a mammalian cell replication origin, and capable of being replicated in a mammalian cell.

4. The vector of claim 1, comprising additionally a transcription terminator segment adjacent the 3' end of the coding segment.

5. A method of expressing a DNA coding segment in yeast, comprising the steps of
    (a) inserting the coding segment in a yeast expression vector, the vector comprising a replication origin functional in yeast and a DNA segment derived from an adenovirus major late promoter, the promoter being adjacent the 5' end of the inserted DNA coding segment and so oriented that transcription initiated within the adenovirus promoter segment includes the coding segment, thereby providing a coding segment expression vector, and
    (b) transforming a yeast cell with the coding segment expression vector, whereby synthesis of protein coded by the coding segment occurs during growth and replication of the transformed yeast cell under normal culture conditions.

6. The method of claim 5, wherein the coding segment codes for hepatitis B surface antigen.

* * * * *